United States Patent [19]

Scholl

[11] 4,394,495
[45] Jul. 19, 1983

[54] DIISOCYANATES USEFUL AS A STRUCTURAL COMPONENT IN THE PREPARATION OF POLYURETHANE PLASTICS

[75] Inventor: Hans-Joachim Scholl, Cologne, Fed. Rep. of Germany

[73] Assignee: Bayer Aktiengesellschaft, Leverkusen, Fed. Rep. of Germany

[21] Appl. No.: 344,120

[22] Filed: Jan. 29, 1982

[30] Foreign Application Priority Data

Feb. 17, 1981 [DE] Fed. Rep. of Germany ....... 3105776

[51] Int. Cl.³ .............................................. C08G 18/76
[52] U.S. Cl. .................................... 528/67; 252/182; 260/453 AR
[58] Field of Search ................ 252/182; 260/453 AR; 528/67

[56] References Cited

U.S. PATENT DOCUMENTS 2,934,571  4/1960  Bonetti ......................... 260/453 AR
2,986,576  5/1961  Bonetti ......................... 260/453 AR
3,652,424  3/1972  Jackson et al. ..................... 252/182

OTHER PUBLICATIONS

ASTM D 86-78, 1978.
Polyurethanes-Chemistry & Technology-Part I, Saunders & Frisch, Interscience Publishers, 1962, pp. 17 et seq.

Primary Examiner—Maurice J. Welsh
Attorney, Agent, or Firm—Gene Harsh; Joseph C. Gil; Lyndanne M. Whalen

[57] ABSTRACT

A mixture of homologues and isomers of hydrocarbons corresponding to the formula

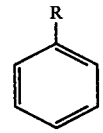

in which R represents a saturated, straight-chained aliphatic hydrocarbon radical having 8–15 carbon atoms, which mixture, at 1013 mbar, has a boiling range according to ASTM D 86 of 10°–50° C. within the temperature range of from 270°–330° C. is nitrated, hydrogenated and phosgenated. The product diisocyanate which is liquid, readily soluble, has a lower vapor pressure than TDI, does not tend to crystallize at room temperature and is virtually free of monoisocyanates is a mixture of homologues and isomers corresponding to the formula

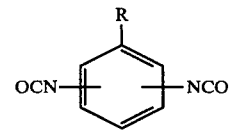

in which R is as defined above. These diisocyanates are particularly useful as starting materials in the production of polyurethane plastics.

2 Claims, No Drawings

DIISOCYANATES USEFUL AS A STRUCTURAL COMPONENT IN THE PREPARATION OF POLYURETHANE PLASTICS

BACKGROUND OF THE INVENTION

The present invention relates to alkyl-substituted diisocyanates in the form of a mixture of homologues and isomers. These alkyl-substituted diisocyanates are useful structural components in the preparation of polyurethane plastic materials by the isocyanate polyaddition process.

Aromatic diisocyanates are known (cf "Polyurethanes", Chemistry and Technology, Part I, by Saunders and Frisch, Interscience Publishers, (1962), pages 17 et seq.). In particular, 2,4- and 2,6-diisocyanato toluenes and mixtures of these isomers ("TDI") and 2,4'- and 4,4'-diisocyanato diphenyl methane and mixtures of these isomers, as well as mixtures of these last-mentioned diisocyanates with high homologues of the type obtained by phosgenation of aniline/formaldehyde condensates ("MDI") are of great commercial importance. The diisocyanato toluenes which are liquid at room temperature have the disadvantage of having a relatively high vapor pressure which makes it necessary to take comprehensive measures during processing in order to keep the TDI concentrations in the air within permissible limits. Another disadvantage of TDI is that the diisocyanato toluene isomers have melting points which are only slightly below room temperature so that at least partial crystallization of the diisocyanate or of the diisocyanate mixtures occurs during storage and during transportation of TDI in cold weather. Such partial crystallization makes it necessary to subject the diisocyanate or the diisocyanate mixtures to a melting process prior to use in polyurethane production. Moreover, although the above-mentioned diisocyanates of the diphenyl methane series have a far lower vapor pressure than TDI, which makes their processing far less problematical from the physiological point of view, these polyisocyanates have the disadvantage that the 4,4'-diisocyanato diphenyl methane present in them as main component is a solid substance at room temperature. These polyisocyanates must, therefore, be melted or liquefied by a chemical reaction before further processing.

U.S. Pat. No. 2,934,571 discloses preparation of long-chained dinitro alkyl benzenes. U.S. Pat. No. 2,986,576 (corresponding to German Auslegeschrift No. 1,123,662) teaches that such dinitro alkyl benzenes can be used to produce the corresponding diamines which may then be converted to the corresponding diisocyanates. The alkyl benzenes used as starting materials in U.S. Pat. No. 2,934,571 (particularly in the Examples) are very specific compounds which have a branched oligopropylene side chain. A special nitration process is described for the nitration of these hydrocarbons because conventional nitration processes obviously fail to nitrate these hydrocarbons into the corresponding dinitro alkyl benzenes. In spite of the complex process (which involves the use of sulfuric acid containing sulfur trioxide) undesirable residual mononitro compounds are formed (note Example 2 infra). The further processing of this disclosed intermediate stage into diisocyanates via the corresponding diamines inevitably leads to diisocyanates in which undesirable monoisocyanates are present. Such monoisocyanates act as chain breakers in the preparation of polyurethane plastics by the isocyanate addition process and lead to unusable products (see Example 2 infra). These difficulties make it clear why the diisocyanates in the above-mentioned disclosures have not been used in commercial polyurethane processes.

SUMMARY OF THE INVENTION

It is an object of the present invention to provide an aromatic diisocyanate in which virtually no monoisocyanates are present.

It is also an object of the present invention to provide an aromatic diisocyanate which has a lower vapor pressure than TDI and which is a liquid having no tendency to crystallize at room temperature.

It is another object of the present invention to provide a relatively simple process for the production of an aromatic diisocyanate which has a lower vapor pressure than TDI and which is liquid at room temperature.

It is a further object of the present invention to provide a process for the production of polyurethane plastic materials in which the reactant isocyanate is an aromatic diisocyanate which is liquid at room temperature and which has a vapor pressure lower than TDI.

These and other objects which will be apparent to those skilled in the art are accomplished by nitrating a mixture of homologues and isomers of hydrocarbons corresponding to the formula

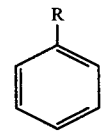

in which R is as defined below and which mixture has a boiling range at 1013 mbar according to ASTM D 86 of 10°–50° C., preferably 20°–30° C., within the temperature range of from 270° C.–330° C. This nitration product is then hydrogenated to form a mixture of diamino compounds which mixture is subsequently phosgenated to yield a mixture of homologues and isomers of diisocyanates corresponding to the formula

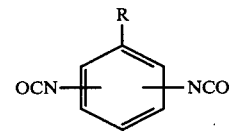

in which R represents a saturated, straight chained aliphatic hydrocarbon radical having 8 to 15 carbon atoms. This diisocyanate mixture is particularly useful as a reactant in known processes for the production of polyurethanes.

DETAILED DESCRIPTION OF THE INVENTION

The present invention relates to a homologue and isomer mixture of diisocyanates corresponding to the formula:

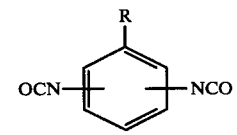

in which R represents a saturated, straight-chained, aliphatic hydrocarbon radical with 8 to 15 carbon atoms. Such a mixture may be obtained by dinitration of hydrocarbons, subsequent hydrogenation of the nitro groups thus introduced to form amino groups and phosgenation of the amino groups thus-formed. The hydrocarbons employed are homologue and isomer mixtures of hydrocarbons corresponding to the formula:

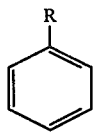

which have a boiling range at 1013 mbar (according to ASTM D 86) of from 10°–50° C., preferably 20°–30° C. within the temperature range of from 270° C.–330° C.

In the preparation of diamines from which the diisocyanates of the present invention are formed, the alkyl benzene used as the starting material is a mixture of homologues and isomers of alkyl benzenes corresponding to the formula:

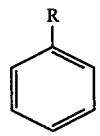

in which R represents a saturated, straight-chained aliphatic hydrocarbon radical having 8 to 15, preferably 10 to 13 carbon atoms. This mixture has a boiling range at 1013 mbar (according to ASTM D 86) of 10°–50° C., preferably 20°–30° C. within the temperature range of from 270° C.–330° C. It is preferable that at least 30% by volume boil below the middle of the boiling range and that at least 30% by volume boil above the middle of the boiling range.

The preparation of such alkyl benzene mixtures may be carried out by methods known to those in the art. One such process is alkylation of benzene with appropriate commercial linear olefin mixtures such as the corresponding commercial oligoethylene mixtures or other linear oligoolefins or with the corresponding commercial linear alkyl chloride mixtures (described, for example, in Kirk-Othmer, Encyclopedia of Chemical Technology, Third Edition, Vol. 2, (1978) on pages 59 to 61).

The diamines to be used in making the diisocyanates of the present invention may be prepared by converting the alkyl benzene(s) into the corresponding dinitro compound(s) by nitration in accordance with techniques known to those in the art. In one such nitration procedure, from 2 to 3 mol of concentrated nitric acid are added for each mol of alkyl benzene while the temperature is maintained at 10°–30° C. The nitric acid used is generally in the form of a mixture with concentrated sulfuric acid (nitrating acid). In the alkyl-substituted dinitro benzenes produced by such process, over 95% of all the nitro groups are in the meta-position relative to each (as determined by nuclear resonance measurement). About 10 to 30 wt. % of the dinitrated alkyl benzenes would be expected to be 1-alkyl-2,6-dinitrobenzenes and about 70 to 90 wt. % should be 1-alkyl-2,4-dinitrobenzenes. However, this isomer distribution is not essential to the present invention and mixtures of dinitrated alkyl benzenes containing different proportions of the above-mentioned isomers may also be used. For example, 1-alkyl-2,4-dinitrobenzene free from the 2,6-isomer could also be used as a starting material for the hydrogenation of the present invention. This dinitrobenzene may be obtained, for example, by two-stage nitration of alkyl benzene in which the 1-alkyl-4-nitrobenzene is isolated from the nitration mixture and then dinitrated. The dinitro compounds prepared in this way from the alkyl benzene mixtures suitable to the practice of the present invention contain no undesirable residual mononitro compounds, and can be further processed into diisocyanates in which virtually no monoisocyanates are present.

The next stage of the present invention is hydrogenation of the dinitro compounds. Appropriate procedures for hydrogenating the nitro groups into the corresponding primary amino groups are known to those in the art. In one such process, Raney nickel is used as the hydrogenation catalyst, the temperature is maintained at 20° to 60° C. and the hydrogen pressure is from 20 to 40 bar. The positions of the amino groups and the R radical of the thus-produced diamines obviously correspond to the positions of the nitro groups and of the R radical in the alkyl benzene used as starting material.

In the preparation of the diisocyanates of the present invention, the liquid, readily soluble diamines thus obtained (a homologue and isomer mixture) are subjected to a phosgenation reaction. Appropriate phosgenation techniques are known to those in the art. In one such procedure, the diamine is dissolved in an auxiliary solvent such as chlorobenzene and added dropwise into a solution of phosgene in chlorobenzene with stirring and cooling at −20° to +5° C. (preferably −10° to 0° C. (cold phosgenation). The reaction mixture is then heated with continued stirring and introduction of phosgene to 80° to 130° C. (preferably 90° to 110° C.) in order to convert the carbamic acid chloride initially formed into the desired diisocyanate (hot phosgenation). The reaction mixture is subsequently worked up in accordance with techniques known to those in the art. The diamines can also be converted into the diisocyanates of the present invention by any of several other phosgenation methods known to those skilled in the art.

The diisocyanates of the present invention are liquid substances which have no tendency to crystallize, which have no significant smell at room temperature and have no undesirable residual monoisocyanates. These diisocyanates are homologue and isomer mixtures of diisocyanates corresponding to the above-described general formula. The position of the isocyanate groups corresponds to that of the nitro groups of the nitration product. The R radical of the diisocyanate has the same meaning as the R group present in the alkyl benzenes used as starting material. The diisocyanates of the present invention are valuable starting materials for the preparation of polyurethane plastic materials by the isocyanate polyaddition process. The diisocyanates of the present invention can be used instead of the aromatic diisocyanates formerly used in the preparation of, for example, polyurethane foams, elastomers, adhesives, dispersions, coatings or lacquers by proceses known to those in the art. Appropriate reactants and auxiliaries are known to those in the art. The diisocyanates of the present invention are also valuable intermediate products for the preparation of pesticides.

The present invention yields monoisocyanate-free, liquid, readily soluble diisocyanate mixtures with a low vapor pressure which do not tend to crystallize in a technically simple manner (i.e., by known nitration, hydrogenation and phosgenation processes) when alkyl benzenes in the form of a homologue and isomer mixture of the type described herein are employed.

The following Examples illustrate the present invention. All percentages relate to percentages by weight, unless otherwise stated. Ready-made TLC plates, silica gel 60 F-254 made by the company Merck AG, were used for the thin layer chromatographic investigations.

EXAMPLES

EXAMPLE 1

A homologue mixture of linear alkyl benzenes in which alkyl chains having a length of 10 to 13 carbon atoms with an average chain length of about 12 carbon atoms was used. The homologue mixture boiled (according to ASTM D 86) at 1013 mbar at between about 283° and 313° C. About 50% by volume distilled over at up to 296° C. This mixture was a reaction product of benzene with a mixture of linear $C_{10}$–$C_{13}$ olefins.

(1a) Nitration of the alkyl benzene mixture

A mixture of 1136 ml of 98% nitric acid and 1584 ml of 96% sulfuric acid was added dropwise to 1,97 kg of the alkyl benzene mixture with cooling in a manner such that the internal temperature was maintained at 10° to 15° C. After this addition, the mixture was stirred for 3 hours at 25° to 30° C. The reaction mixture was then poured on 10 kg of ice, and the organic phase was washed neutral with sodium bicarbonate solution and again washed with water. The organic phase was then separated and substantially freed from any residues of water by centrifugation. The liquid dinitro alkyl benzene mixture thus obtained was used without further purification for the next stage of the reaction.

Yield: 2.7 kg; $NO_2$-content: 27.5% (Theoretical: 27.4%). No residual mononitro compounds could be detected by thin layer chromatographic investigations (eluent 90 parts by weight petroleum ether/10 parts by weight ether).

(1b) Hydrogenation of the dinitro alkyl benzene mixture 672 g of the dinitro compounds prepared in (1a) were dissolved in 1700 ml of ethanol and mixed with 70 g of Raney nickel in a stirrer autoclave. The mixture was stirred at 40° C. and 20 to 40 bar hydrogen pressure until absorption of hydrogen ceased. The pressure was then released, the catalyst was filtered off and the ethanol was distilled off. 550 g of crude amine mixture was obtained which was used in (1c) without being worked up by distillation. The crude amine mixture had a nitrogen content of 10.06% (Theoretical: 10.1%).

(1c) Phosgenation of the crude amine mixture 3 l of dry chlorobenzene were placed in a 6 l four-necked flask provided with a stirrer, thermometer, gas inlet tube and reflux condenser. About 800 g of phosgene were condensed in this flask with stirring and cooling (−10° C.). 550 g of crude amine mixture prepared in (1b) dissolved in 500 ml chlorobenzene were then added dropwise with cooling at −10° to −5° C. With continued introduction of phosgene, the solution heated up to about 30° C. Once the heat of reaction had dissipated, the mixture was heated slowly to 100° C. and phosgene was introduced until hydrogen chloride evolution ceased (total 970 g). The excess phosgene was blown out with nitrogen and the solution was evaporated in vacuo. 638 g of crude isocyanate mixture with an NCO content of 25% was obtained (Theoretical: 25.6%). The diisocyanate thus obtained could be used without further purification as a starting material for the preparation of polyurethanes but it was further purified by distillation. 300 g of the diisocyanate mixture were distilled under a reduced pressure. At a pressure of 2.2 mbar and a temperature within the range of 185° to 203° C., 273 g of a virtually colorless mixture of diisocyanates corresponding to the formula:

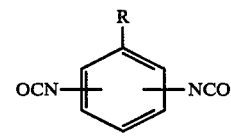

distilled over. These diisocyanates showed no tendency to crystallize even on cooling to −50° C. The product diisocyanate had the following analysis:

|  | % NCO | % C | % H | % N |
|---|---|---|---|---|
| Determined: | 25.5 | 73.6 | 8.6 | 8.4 |
| Theoretical (based on $C_{20}H_{28}N_2O_2$) | 25.6 | 73.2 | 8.5 | 8.5 |

According to nuclear resonance measurement, the isocyanate group of the diisocyanate were in the meta position relative to each other. The main component of the mixture was 1-alkyl-2,4-diisocyanato-benzene.

EXAMPLE 2 (Comparison Example)

(2a) A dodecyl phenylene diisocyanate was prepared according to Example V of U.S. Pat. No. 2,934,571 and Examples V and VI of U.S. Pat. No. 2,986,576. The NCO content determined in the diisocyanate prepared in this way was 20.2%. The low NCO content is attributable to the incomplete dinitration of the dodecyl benzene used. Thin layer chromatographic investigations showed significant amounts of mononitro compounds.

(2b) Two prepolymers were prepared using the diisocyanate mixture of Example 1 and the diisocyanate of (2a) respectively:

0,25 mol of a polyester having an OH number of 45, prepared from adipic acid and diethylene glycol, and 0,5 mol of each diisocyanate were reacted in both cases at 80° C. until the NCO content of the reaction mixture was constant. The prepolymers were each dissolved in DMF-toluene (1:1) to form 65% solutions and then mixed dropwise with about 42 g of IPDA with stirring at room temperature (NCO/$NH_2$ equivalent ratio of about 1:1). After the disappearance of the NCO band in the IR spectrum, each mixture was adjusted to a 50% solution in DMF/toluene/isopropanol by addition of isopropanol.

The solution of the polyurethane polyurea prepared in this way using the diisocyanate mixture from Example 1 had a viscosity of 25,000 mPa.s/20° C. A solvent-free film of polyurethane polyurea prepared from the solution was dry, non-tacky and had a tensile strength of 10.4 mPa. The solution of the polyurethane polyurea prepared using the diisocyanate of (2a), on the other hand, had a viscosity of only 400 mPa.s/20° C. Attempts to produce a dry film from this solution led to a smeary, blurred coating having no mechanical strength.

EXAMPLE 3

The diisocyanate mixture from Example 1 was used to produce a polyurethane two-component lacquer which could advantageously be used in a solvent consisting largely of aliphatic hydrocarbons. In preparing the lacquer, a binder containing hydroxyl groups and an alkyd resin made of 1.6 mol of phthalic acid anhydride, 2.7 mol of trimethylol propane, 0.6 mol of adipic acid, 1.35 mol of soya oil fatty acid (average molecular weight about 290) and 0.16 mol of maleic acid (prepared by conventional melt condensation) were employed.

This polyester resin had a hydroxyl number of 110 and an acid number of 7 and was dissolved to form a 50% solution in a 5:2 mixture of white spirit/xylene.

A lacquer having the following composition was prepared from the polyester resin using various auxiliary products:
Polyester resin (50%) in petrol/xylene 5:2): 300.0 parts by weight
TiO$_2$ pigment (Rutile type): 90.0 parts by weight
Zinc octoate (8% metal) as catalyst: 0.6 parts by weight
Anti-skinning agent (butanone oxime): 1.5 parts by weight
Silicone flowing agent 1%: 4.0 parts by weight
These constituents were mixed and the pigment incorporated by means of a sand mill.

To the ground material there was added, with thorough stirring, a 50% solution of 49 parts of the isocyanate mixture from Example 1 in white spirit (corresponding to an OH:NCO ratio of about 1). The lacquer mixture had a processing time of more than 24 hours, in which the viscosity remained virtually unchanged. The viscosity then increased slowly, but the lacquer mixture remained uniform without swollen bodies or deposits being formed and could be reprocessed with white spirit after dilution.

The lacquer was applied using a roller coating system or with an airless injection device in a wet layer thickness of about 100μ to degreased steel sheets and cured. Pure white highly lustrous lacquer films were obtained after drying for 20 to 30 minutes at 80° C. They had an excellent resistance to solvents (5 minutes action of toluene - no change), high elasticity (Erichsen deep drawing DIN 53 156 - 100 mm/sheet tear) and excellent hardness (Pendulum hardness DIN 53 157–160 seconds).

In comparison with this lacquer made with the isocyanate mixture of the present invention, attempts were made to incorporate into the same mixture the corresponding molar quantities of 4,4'-diphenyl methane diisocyanate and a mixture (80:20) of 2,4- and 2,6-diisocyanato toluene. This was not possible with 4,4'-diphenyl methane diisocyanate because this diisocyanate dissolves in white spirit only with heating. Such heating, in combination with the polyester solution, resulted in an inhomogeneous mixture from which a precipitate separated after a short time. Although diisocyanato toluene could be mixed homogeneously with the polyester, marked cloudiness also appeared after a short time. The clear lacquer films were inhomogeneous after drying at 80° C. and the films pigmented with TiO$_2$ had no lustre. Apart from this disadvantage, diisocyanato toluene was unsuitable for two-component lacquers due to its high vapor pressure and unpleasant smell.

If, instead of mineral spirit, a polar solvent such as ethylene glycol acetate was added to the two-component lacquer containing diisocyanato toluene, lustrous lacquer films were obtained.

What is claimed is:

1. A mixture of homologues and isomers of diisocyanates corresponding to the formula:

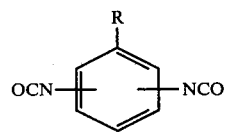

in which R represents a saturated, straight-chained aliphatic hydrocarbon radical having 8 to 15 carbon atoms prepared by
   (a) dinitrating a mixture of homologues and isomers of hydrocarbons corresponding to the formula

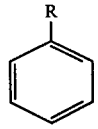

which mixture, at 1013 mbar, has a boiling range according to ASTM D 86 of 10°–50° C. within the temperature range of from 270°–330° C.;
   (b) hydrogenating the product of (a) to form a mixture of diamino compounds; and
   (c) phosgenating the diamino compounds of (b).

2. A process for the production of polyurethane plastic materials by the polyaddition process in which an isocyanate and a polyhydroxyl compound are reacted wherein the isocyanate is a mixture of homologues and isomers of diisocyanates corresponding to the formula:

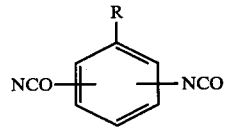

in which R represents a saturated, straight-chained aliphatic hydrocarbon radical having 8 to 15 carbon atoms which mixture is prepared by nitrating, hydrogenating and phosgenating a mixture of alkylbenzenes having, at 1013 mbar, a boiling range according to ASTM D 86 of 10°–50° C. within the temperature range of from 270°–330° C.

* * * * *